United States Patent [19]

Shimizu et al.

[11] Patent Number: 5,780,716
[45] Date of Patent: Jul. 14, 1998

[54] GAS ANALYZING APPARATUS

[75] Inventors: Naohito Shimizu; Shigeyuki Akiyama; Masahiko Fujiwara; Satoshi Inoue; Takuji Oida, all of Miyanohigashi-machi, Japan

[73] Assignee: Horiba, Ltd., Kyoto, Japan

[21] Appl. No.: 702,756

[22] Filed: Aug. 22, 1996

[30] Foreign Application Priority Data

Aug. 24, 1995 [JP] Japan .................... 7-240651

[51] Int. Cl.⁶ .................................. G01N 21/00
[52] U.S. Cl. .......................... 73/23.2; 250/373
[58] Field of Search .................. 73/23.41, 23.42, 73/23.2, 864.91; 250/365, 364, 372, 373, 432 R, 379; 356/435, 437, 440

[56] References Cited

U.S. PATENT DOCUMENTS 3,498,106  3/1970  Fuller et al. .................. 73/23.42
3,845,309  10/1974  Helm et al. ..................... 250/372
4,285,245  8/1981  Kennedy ......................... 73/861
4,388,411  6/1983  Lovelock ....................... 250/379
5,357,809  10/1994  Vander Heyden .............. 73/861.02
5,542,284  8/1996  Layzell et al. ................. 73/23.2

Primary Examiner—Hezron E. Williams
Assistant Examiner—Nashmiya Fayyaz
Attorney, Agent, or Firm—Oppenheimer Wolff & Donnelly LLP

[57] ABSTRACT

A gas analyzing apparatus includes a sample gas line with a sample line valve for providing a sample gas, and a reference gas line with a reference line valve for providing a reference gas. A first gas analyzer is connected to the sample line downstream of the sample line valve, and a second gas analyzer is connected to both the sample and reference gas lines downstream of the valves. The lines are configured such that sample gas and reference gas may be alternately provided to the second gas analyzer either directly or indirectly via the first gas analyzer.

5 Claims, 3 Drawing Sheets

GAS ANALYZING APPARATUS

BACKGROUND OF THE INVENTION

1. Field of the Invention

The present invention relates to a gas analyzing apparatus for measuring by alternately feeding a sample gas and a reference gas, and more particularly to a gas analyzing apparatus capable of analyzing in one method of analysis or in plural combinations of different methods of analysis.

2. Description of the Prior Art

Explaining, for example, the ultraviolet gas analysis method (NDUV method) and infrared gas analysis method (NDIR method), the NDUV method makes use of the characteristic that the gas to be analyzed absorbs ultraviolet rays in an intrinsic wavelength region, and the NDIR method also makes use of the characteristic that the gas to be analyzed absorbs infrared rays in an intrinsic wavelength region.

That is, in the case of NDUV method, as shown in FIG. 4, a solenoid valve 12 is disposed in a line 1 for feeding sample gas, and a solenoid valve 14 is also disposed in a line 3 for feeding reference gas; therefore, the sample gas and reference gas are fed into an NDUV gas analyzer 6 including an ultraviolet ray source, a filter, and a detector. The ultraviolet absorption spectrum is analyzed, and qualitative analysis or quantitative analysis of the object gas is conducted. In the case of NDIR method, on the other hand, as shown in FIG. 3, a solenoid valve (three-way valve) 2 is disposed in a line 1 for feeding sample gas, and a solenoid valve (three-way valve) 4 is also disposed in a line 3 for feeding reference gas. Lines 5 and 7 are arranged so that the sample gas and reference gas may flow into other lines from these two solenoid valves 2 and 4; therefore, the sample gas and reference gas are fed alternately to an infrared gas analyzer 8 including an infrared ray source, a sample cell, a filter, and a detector. The infrared absorption spectrum is analyzed, and qualitative analysis or quantitative analysis of the object gas is conducted.

Thus, hitherto, when analyzing the sample gas, if the principle of measurement is different, individual sample gas lines are provided and separate units are built up, and one gas analyzer was used for each object gas. However, for example, when sulfurous acid ($SO_2$) is analyzed by the NDUV method and carbon monoxide (CO) is analyzed by the NDIR method, two gas analyzers are needed for analyzing stack flue gas which contains both $SO_2$ and CO gases, and they may be analyzed separately. It is also costly because the piping and parts in the unit of these gas analyzers must be composed and assembled for each gas to be measured. In actual measurement, moreover, a large space for the plurality of gas analyzers is needed for arranging the gas analyzers side by side.

SUMMARY OF THE INVENTION

In the light of the above problems, it is hence a primary object of the invention to present a gas analyzing apparatus capable of analyzing two or more types of gas by using analyzers differing in the principle of measurement in one sample gas line, curtailing the number of parts, reducing the cost, and further saving the space for installation.

That is, to solve the problems, the invention presents a gas analyzing apparatus in which a gas analyzer is disposed at either one or both of a sample gas line and a reference gas line. The sample gas line and reference gas line are connected to another gas analyzer. In the sample gas line and reference gas line, a valve is provided for feeding sample gas and reference gas alternately to the latter gas analyzer directly or through the former gas analyzer. The invention also presents a gas analyzing apparatus in which the gas analyzer disposed at either one or both of the sample gas line and reference gas line is provided in plurality.

This analyzing apparatus makes use of a physical measuring method which does not cause changes in the sample gas. Further, for either of the gas analyzing apparatus set forth above, plural gas analyzers of high sensitivity for multiple components can be composed in one sample gas line and reference gas line, so that two or more components of sample gas can be analyzed simultaneously.

DETAILED DESCRIPTION OF THE PREFERRED EMBODIMENTS

Figure 1:
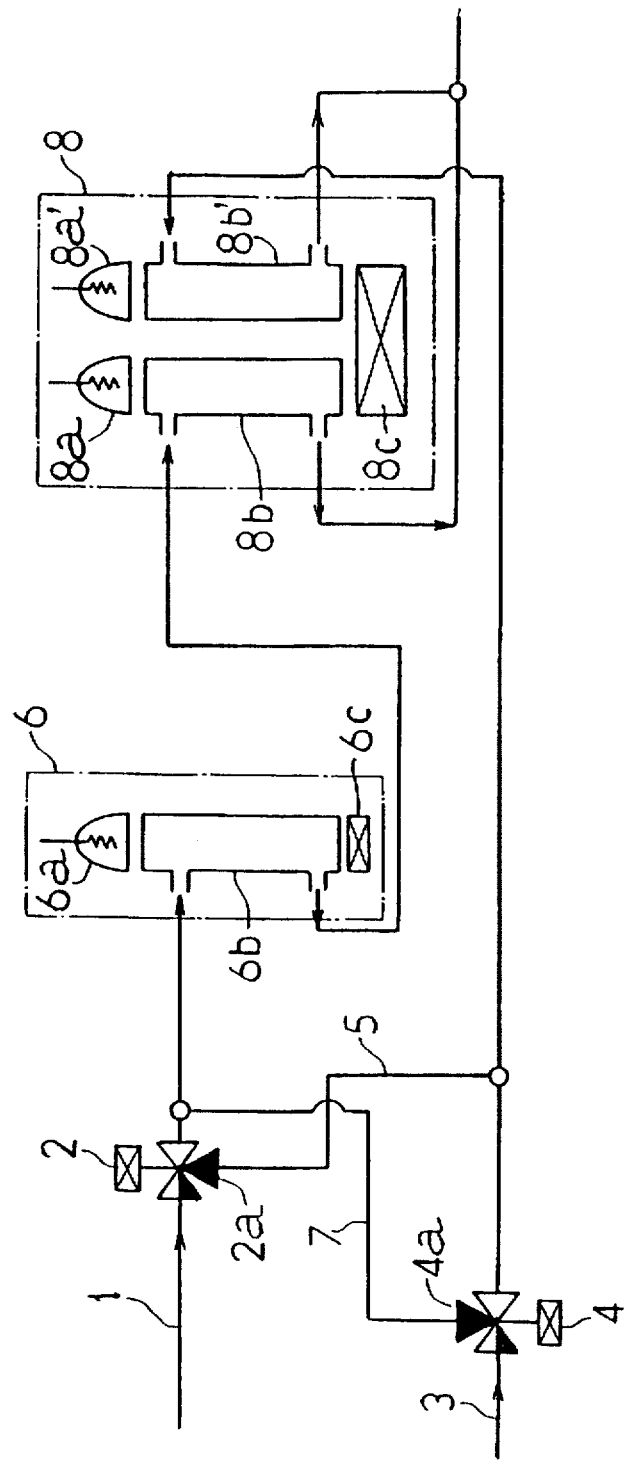
FIG. 1 is a schematic diagram showing a constitution of a first embodiment of a gas analyzing apparatus of the invention.

Referring now to the drawings, preferred embodiments of the invention are described in detail below. FIG. 1 is a diagram showing a constitution of a first embodiment of a gas analyzer of the invention. To avoid duplicated explanation, the same elements as explained in the prior art are identified with same reference numerals. This gas analyzer is an analyzer of a fluid modulation system for feeding sample gas and reference gas alternately. A gas changeover solenoid valve (three-way valve) 2 is disposed in a line 1 for sample gas. Line 1, moreover, is provided with a sample cell 6b of small volume of an ultraviolet analyzer (hereinafter NDUV gas analyzer) 6 and one sample cell 8b of a non-dispersion type infrared analyzer of high sensitivity (hereinafter NDIR gas analyzer) 8. In a line 3 for reference gas, a gas changeover solenoid valve (three-way valve) 4 is disposed, and also an other sample cell 8b of the NDIR gas analyzer 8 is disposed.

At a port 2a of the gas changeover solenoid valve 2, a line 5 connected to the reference gas line 3 is connected, and at a port 4a of the gas changeover solenoid valve 4, a line 7 connected to the sample gas line 1 is connected. Therefore, when the gas changeover solenoid valve 2 is operated, the sample gas is alternately supplied into the line 1 for sample gas and line 3 for reference gas. Similarly, when the gas changeover solenoid valve 4 is operated, the reference gas is alternately supplied into the line 3 for reference gas and line 1 for sample gas.

The NDUV gas analyzer 6 is composed of ultraviolet ray source 6a, sample cell 6b, and detector 6c (filters and other elements are not shown). By alternately feeding sample gas and reference gas into the sample cell 6b, ultraviolet ray absorption of the target component in the sample gas (for example, $SO_2$) is measured. The NDIR gas analyzer 8 is composed of infrared ray sources 8a, 8a', sample cells 8b, 8b', and detector 8c (filter and others are not shown). By alternately feeding sample gas and reference gas into the two sample cells 8b and 8b', infrared absorption of the target component in the sample gas (for example CO) is measured. Incidentally, instead of the gas changeover solenoid valves 2, 4, the gases may be supplied into the NDUV gas analyzer 6 and NDIR gas analyzer 8 by rotary-type valves.

In the gas analyzer of the invention thus constituted, by feeding sample gas from the line 1 for sample gas and feeding reference gas from the line 3 for reference gas, when the gas changeover solenoid valves 2 and 4 are put in operation, the gas having an absorption band in a specific wavelength region of ultraviolet rays can be analyzed in the NDUV gas analyzer 6, while, at the same time, using the sample gas and reference gas, the gas having an absorption band in a specific wavelength region of infrared rays can be measured in the NDIR gas analyzer 8.

Figure 2:
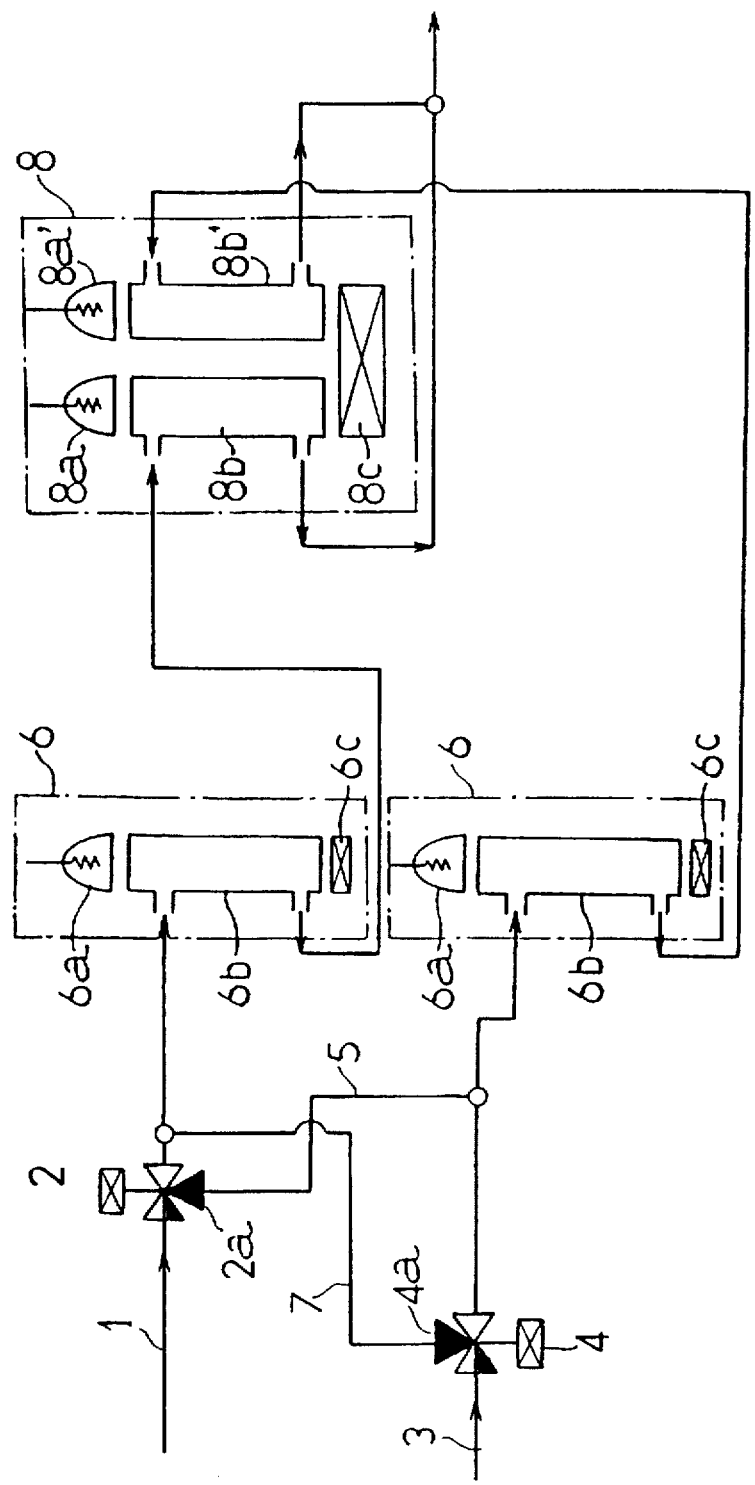
FIG. 2 is a schematic diagram showing a constitution of a second embodiment of a gas analyzing apparatus of the invention.
Figure 3:
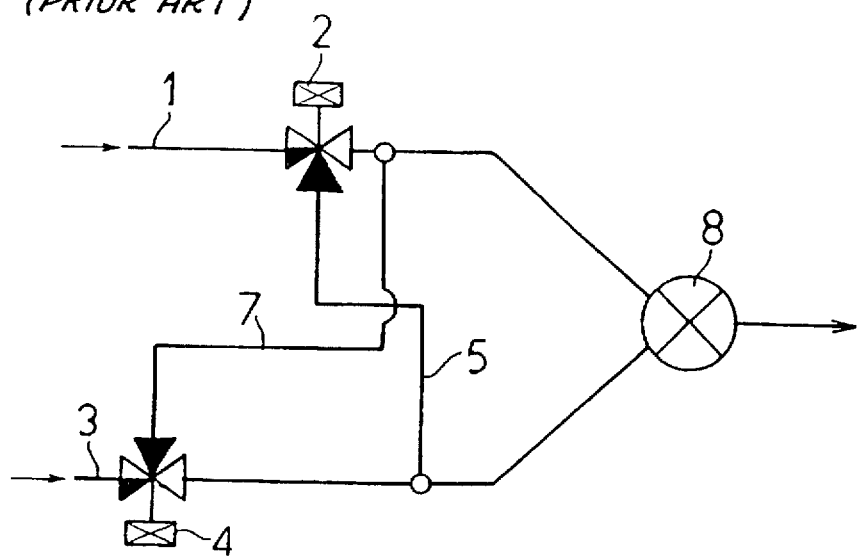
FIG. 3 is a schematic diagram showing a constitutional example of a conventional infrared gas analyzing apparatus by NDIR method and according to prior art.
Figure 4:
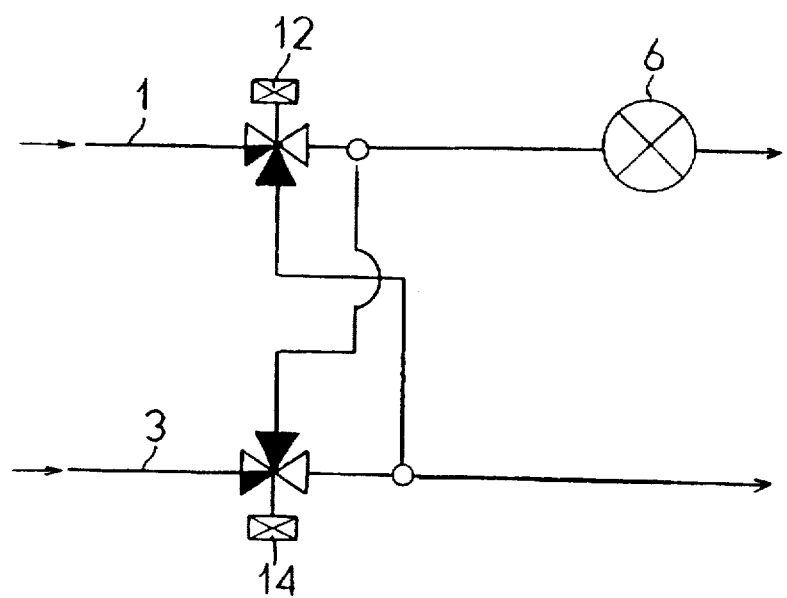
FIG. 4 is a schematic diagram showing a constitutional example of a conventional ultraviolet gas analyzing apparatus by NDUV method according to prior art.

FIG. 2 is a diagram showing a constitution of a second embodiment of a gas analyzer of the invention. In this embodiment of a gas analyzer, the NDUV gas analyzer 6 is disposed in the line 1 for sample gas, and one sample cell 8b of the NDIR gas analyzer 8 is also disposed. In the line 3 for reference gas, moreover, the NDUV gas analyzer 6 is disposed, and an other sample cell 8b of the NDIR gas analyzer 8 is also disposed. In this combination, different types of gas components having absorption and in the wavelength region of ultraviolet rays can be measured by two NDUV has analyzers 6, 6. Simultaneously, gas components having an absorption band in the wavelength region of infrared rays can be measured by the NDIR gas analyzer 8. Using two NDUV gas analyzers 6, 6, if one fails, the other can be used for analysis. Also, trouble can be discovered early if the numerical values are different when the same gas is measured by two NDUV gas analyzers 6, 6. Still further, in these two NDUV gas analyzers 6, 6, they can be calibrated with each other by using span gas, and the reliability of the analyzer is assured.

Thus, according to the gas analyzer of the invention, in either one or both of the line for sample gas and the line for reference gas, the NDUV gas analyzer(s) 6 (6) is disposed, and also the NDIR gas analyzer 8 is disposed. Moreover, in either one or both of the line 1 for sample gas and the line 3 for reference gas, three, four, or more NDUV gas analyzers 6 may be disposed. The infrared gas analyzer such as NDIR gas analyzer 8 may be also provided in plurality. Thus, by disposing plural NDUV gas analyzers and plural NDIR gas analyzers 8, multiple components can be analyzed simultaneously as analyzers of high sensitivity and multiple components.

Not only is the combination of NDIR and NDUV analyzers applicable, but also a chemical luminescence gas analyzer (CLD), a hydrogen ionization gas analyzer (FID), an ultraviolet fluorescent gas analyzer (UVF), a magnetic oxygen meter, and so on, are applicable to the gas analyzer for measuring by alternately feeding sample gas and reference gas in any combination. However, the analyzer initially disposed in the line and initially used for measurement is limited only to the measuring method without altering the sample gas or reference gas by chemical reaction or the like.

According to the gas analyzing apparatus of the invention as described herein, if using gas analyzers differing in the principle of measurement, multiple gas components can be analyzed simultaneously by one gas analyzing apparatus. Hitherto, in different methods of analysis, different gas analyzers were used, but by the gas analyzing apparatus of the invention, only one gas analyzing apparatus is enough, the number of parts is decreased, and the manufacturing cost is lowered. At the same time, the space for installation is saved for gas analysis. Moreover, plural gas analyzers of same type are used and if one is defective, analysis can continue, or a defective analyzer can be detected promptly.

What is claimed is:

1. A gas analyzing apparatus comprising:

a sample gas line having a sample line valve for controlling a supply of a sample gas flowing in the sample gas line;

a reference gas line having a reference line valve for controlling a supply of a reference gas flowing in the reference gas line;

a first gas analyzer connected to the sample gas line downstream of the sample line valve; and a second gas analyzer connected to the sample gas line downstream of the first gas analyzer and connected to the reference gas line downstream of the reference line valve; and a third gas analyzer connected to the sample line valve and connected to the reference gas line between the reference line valve and the second gas analyzer;

the sample line valve being connected to the reference gas line upstream of the second gas analyzer;

the reference line valve being connected to the sample gas line upstream of the first gas analyzer;

the sample line valve and the reference line valve selectively supplying the sample gas and the reference gas to the second gas analyzer either directly or indirectly via the first gas analyzer;

the sample line valve and the reference line valve selectively supplying the sample gas and the reference gas to the second gas analyzer via either the first gas analyzer or the third gas analyzer; and the first gas analyzer and the third gas analyzer each including an ultraviolet source, and the second gas analyzer including an infrared source.

2. A gas analyzing apparatus comprising:

a sample gas line having a sample line valve for controlling a supply of a sample gas flowing in the sample gas line;

a reference gas line having a reference line valve for controlling a supply of a reference gas flowing in the reference gas line;

a first gas analyzer connected to the sample gas line downstream of the sample line valve; and a second gas analyzer connected to the sample gas line downstream of the first gas analyzer and connected to the reference gas line downstream of the reference line valve;

the sample line valve being connected to the reference gas line upstream of the second gas analyzer;

the reference line valve being connected to the sample gas line upstream of the first gas analyzer;

the sample line valve and the reference line valve selectively supplying the sample gas and the reference gas to the second gas analyzer either directly or indirectly via the first gas analyzer; and the second gas analyzer including:
a first sample cell connected to the sample gas line; and
a second sample cell connected to the reference gas line.

3. A gas analyzing apparatus capable of selectively supplying a sample gas and a reference gas to a gas analyzer, the gas analyzing apparatus comprising:

a sample gas line for receiving a sample gas;

a reference gas line for receiving a reference gas;

a sample line valve disposed in the sample gas line and including a port, the sample line valve for selectively supplying the sample gas to the sample gas line downstream of the sample line valve or to the port of the sample line valve;

a reference line valve disposed in the reference gas line and including a port, the reference line valve for selectively supplying the reference gas to the reference gas line downstream of the reference line valve or to the port of the reference line valve;

a first line having an inlet connected to the port of the sample line valve and an outlet connected the reference gas line downstream of the reference line valve;

a second line having an inlet connected to the port of the reference line valve and an outlet connected to the sample gas line downstream of the sample line valve;

a first gas analyzer including a sample cell having an inlet connected to the sample gas line downstream of the outlet of the second line, the sample cell having an outlet; and a second gas analyzer including:

a first sample cell having an inlet connected to the outlet of the sample cell of the first gas analyzer, the first sample cell having an outlet; and a second sample cell having an inlet connected to the reference gas line downstream of the outlet of the first line, the second sample cell having an outlet;

whereby the sample line valve is capable of selectively supplying the sample gas directly to the second sample cell of the second gas analyzer and indirectly to the first sample cell of the second gas analyzer via the first gas analyzer; and whereby the reference line valve is capable of selectively supplying the reference gas directly to the second sample cell of the second gas analyzer and indirectly to the first sample cell of the second gas analyzer via the first gas analyzer.

4. A gas analyzing apparatus as claimed in claimed 3 further comprising a third gas analyzer including a sample cell having an inlet connected to the reference gas line downstream from the outlet of the first line and having an outlet connected to the inlet of the second sample cell of the second gas analyzer.

5. A gas analyzing apparatus as claimed in claim 4 wherein the first gas analyzer and the second gas analyzer each include an ultraviolet source, and the second gas analyzer includes an infrared source.

* * * * *